(12) United States Patent
Gupta

(10) Patent No.: US 6,478,930 B2
(45) Date of Patent: *Nov. 12, 2002

(54) IMPURITIES SEPARATION BY DISTILLATION

(75) Inventor: Vijai P. Gupta, Berwyn, PA (US)

(73) Assignee: Arco Chemical Technology, L.P., Greenville, DE (US)

(*) Notice: Subject to any disclaimer, the term of this patent is extended or adjusted under 35 U.S.C. 154(b) by 0 days.

This patent is subject to a terminal disclaimer.

(21) Appl. No.: 09/938,012

(22) Filed: Aug. 23, 2001

(65) Prior Publication Data

US 2002/0000366 A1 Jan. 3, 2002

Related U.S. Application Data

(63) Continuation of application No. 09/283,110, filed on Mar. 31, 1999, now Pat. No. 6,306,263.

(51) Int. Cl.[7] .......................... B01D 3/38; C07C 27/28; C07C 29/20; C07C 31/18
(52) U.S. Cl. .................. 203/96; 203/97; 203/98; 203/100; 568/868
(58) Field of Search ................ 203/91–96, 97, 203/98, 100, 18, 21, DIG. 9; 568/868, 913

(56) References Cited

U.S. PATENT DOCUMENTS

| 3,418,338 A | * | 12/1968 | Gilman et al. ............... 203/93 |
| 4,134,797 A | * | 1/1979 | Ozaro ........................ 203/82 |
| 4,140,588 A | * | 2/1979 | Schmidt ..................... 203/92 |
| 4,277,311 A | | 7/1981 | Kwasnoski et al. |
| 4,359,365 A | | 11/1982 | Deguchi et al. |
| 4,695,349 A | * | 9/1987 | Becker et al. ............... 203/26 |
| 4,789,554 A | | 12/1988 | Scavone et al. |
| 4,917,769 A | | 4/1990 | Van Horn |
| 4,983,329 A | | 1/1991 | Cooper |
| 5,013,572 A | | 5/1991 | Hay |
| 5,268,510 A | | 12/1993 | Schwab et al. |
| 5,529,667 A | * | 6/1996 | Coffey ....................... 203/96 |
| 5,817,889 A | | 10/1998 | Pondebat et al. |

FOREIGN PATENT DOCUMENTS

GB 1180822 * 2/1970

* cited by examiner

Primary Examiner—Virginia Manoharan
(74) Attorney, Agent, or Firm—William C. Long

(57) ABSTRACT

A distillation procedure is provided for the separation of impurities from organic materials such as glycols and glycol ethers whereby a liquid stripping component is interfaced into a distillation column with or below the organic material introduction, heat being provided by a reboiler, the stripping component and impurities being removed overhead.

2 Claims, 1 Drawing Sheet

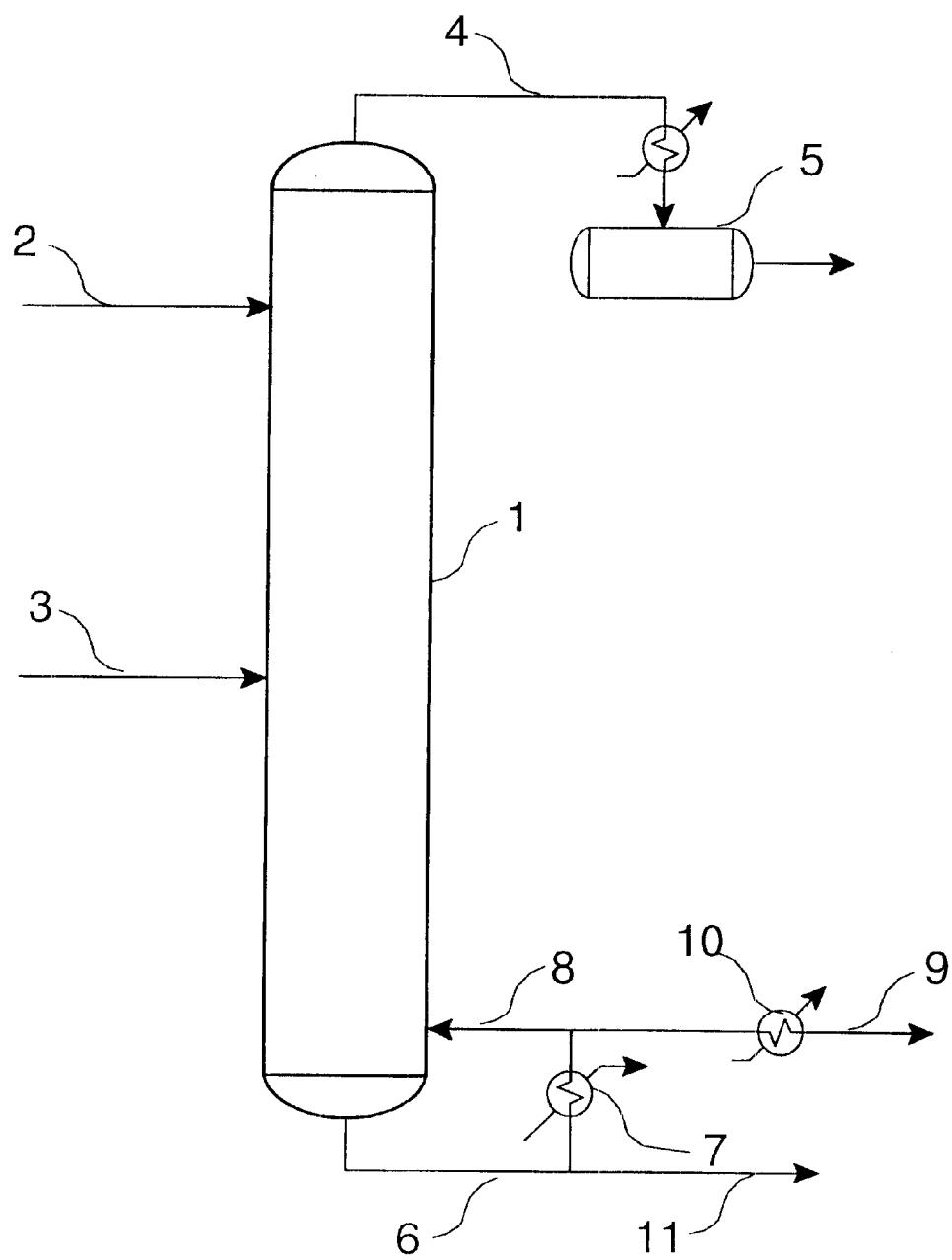

IMPURITIES SEPARATION BY DISTILLATION

This is a continuation of application Ser. No. 09/283,110, filed Mar. 31, 1999, now U.S. Pat. No. 6,306,263 B1.

BACKGROUND ON THE INVENTION

1. Field of Invention

The present invention relates to the separation of minor amounts of impurities from organic products such as glycols, glycol ethers, hydrocarbons and the like by an improved distillation procedure.

2. Description of the Prior Art

During normal preparation procedures, various oxygenated derivatives of organic products such as glycols, glycol ethers, glycol ether esters, hydrocarbons and the like, are formed in very small amounts especially at the elevated distillation temperatures which are normally employed in the production of such products. These impurities are frequently aldehydes, ketones, acids and the like and are undesirable in the product in that they impart characteristics such as malodor to the product.

Various methods are known for separating minor amounts of impurities, especially close boiling impurities, from various products including azeotropic and extractive distillation procedures but such prior methods are generally complicated and expensive. Steam stripping techniques have been employed but tend to result in the introduction of unwanted impurities with the steam, as well as producing water enriched products.

Stripping with inert gas, eg. nitrogen, produces a non-condensible stream which, if vented to the atmosphere would add to pollution, and if flared, adds a large load to the flare system. Also the inert gas does not enhance the volatilities of impurities.

Now, in accordance with the present invention there is provided a simple and effective distillation procedure whereby the separation of minor amounts of impurities is achieved.

BRIEF DESCRIPTION

In accordance with the invention, the organic mixture to be purified is fed to the upper section of a fractional distillation column, while a stripping component such as water or methanol in liquid form is fed to the column with the organic mixture to be purified or at a point below the point of introduction of the mixture to be purified. A reboiler is provided wherein bottoms from the column is vaporized and circulated to the column thus providing heat to the column. Heat input into the column via reboiler vapors is sufficient to ensure vaporization of the liquid stripping component stream introduced to the column, and the pressure maintained in the column is effective to prevent overheating especially in the reboiler, while maintaining stripping vapor flow upwardly through the column. The stripping component, eg. water, plus the undesirable impurities are removed overhead, organic product substantially reduced in impurities is removed as bottoms.

BRIEF DESCRIPTION OF THE DRAWING

The attached drawing illustrates schematically practice of the invention.

DETAILED DESCRIPTION

A number of relatively high boiling organic products as produced are contaminated with minor quantities of close boiling and usually lighter components. Examples of relatively high boiling products include glycols, glycol ethers, propylene carbonate, mineral oils, styrene, and the like. The impurities generally are oxygenated derivatives of such products. The present invention provides a method for removing associated minor impurities by a simple and straight forward distillation procedure.

The invention can, perhaps, best be described with reference to the attached drawing in the context of the separation of minor impurities from glycol ethers. Referring to the drawing, distillation column 1 represents a multi stage fractional distillation column. Introduced to column 1 at a point near the top via line 2 is a product comprised mainly of di-propylene glycol n-butyl ether contaminated with small amounts of impurities. Introduced into column 1 via line 3 near the middle of the column is a liquid stripping component stream, preferably a water or methanol stream. Vacuum or in some cases pressure depending on the material being separated is applied to the column in order to maintain a temperature in the reboiler at a point which will not cause substantial degradation of the organic feed. Generally, it is advantageous to maintain conditions such that the reboiler temperature does not exceed about 175° C. A further important consideration is that sufficient heat is supplied to the column via the reboiler vapors to ensure that the liquid stripping component stream introduced via line 3 is vaporized in the distillation column. It is generally desirable to maintain a pressure of 50 mm Hg or more at the top of the column in order to provide for easy condensation of the stripping component with cooling tower water and to keep the reboiler at generally acceptable temperatures.

Heat input via the reboiler is provided such that the temperatures in the column near the top are closer to the boiling point of the stripping component, eg.water, than to the boiling point of the organic material which is to be purified at the pressure in the column. Specifically, the boil up of the product in the reboiler is maintained such that all the stripping component introduced as liquid via line 3 vaporizes and the heat losses are accounted for. There is no external reflux of significance at the top of the column. There is, however, a good deal of internal reflux in the column at the stripping component introduction point.

While it is not desirable to provide reflux to the top of the column, this may be done for ease of operation.

Below the stripping component introduction point in the column, heated organic product vapors rising from the reboiler strip the down coming organic materials and the stripping action is assisted by stripping component present at the injection point and below. Above the stripping component injection point, lower temperature stripping vapor rising through the column strips the down coming product removing lights and some heavies whose volatility relative to the product is enhanced by the stripping component vapor. Temperatures in the column above the stripping component injection point are low so the vapor does not carry much of the product upwardly. Stripping component vapor along with various impurities is removed from the column via line 4 and condensed using tower water.

The bottoms stream is removed as liquid from the column via line 6 and most passes to reboiler 7 wherein the organic stream is heated. A portion of vapors is returned via line 8 to column 1 and the remaining portion is removed as product passing via line 9 to condenser 10 for recovery of the purified organic product. A small purge stream is removed via line 11 if desired. If condenser 10 is not available, product may be withdrawn via line 11.

Generally, the liquid stripping component is used in amount of about 2–25% by weight based on the feed, preferably about 5–10 wt %.

EXAMPLE 1

By way of illustration in a specific practice of the present invention, a product stream mainly comprised of di-propylene glycol n-butyl ether is purified by the procedure of the present invention. A stream comprised of 99% pure di-propylene glycol n-butyl ether but having an uncharacteristic malodor due to the presence of small amounts of impurities is introduced into column 1 via line 2 at the rate of 25 lbs per hr. Column 1 is a fractionation column containing 30 theoretical distillation stages. The organic stream introduced via line 2 enters the column at the 7th stage from the top. Also introduced into column 1 via line 3 is a liquid water stream which is introduced at the rate of 4 lbs per hr. and enters column 1 at a point 15 stages from the bottom.

Column 1 is maintained at an overhead pressure of 70 mm. Hg and temperature of 130–140° F. Upon entering the column, the liquid water is immediately vaporized in the section in which it is introduced, the vaporization causing substantial internal condensation and reflux of the materials which are contained in the column. The heavier di-propylene glycol n-butyl ether component flows downwardly through the column and is removed via line 6. Reboiler temperature is about 316° F. From the reboiler all the organic vapors are circulated via line 8 back to the bottom of column 1 thus providing organic stripping vapor in the lower section of column 1 and the heat needed to operate the distillation. A net purified product is removed via line 11. The net product is recovered at the rate of 25 lbs per hr.

In column 1, the vaporized water passing upwardly through the column strips from the downwardly flowing organic materials the impurities which were associated with the di-propylene glycol n-butyl ether feed stream and a vapor stream is removed overhead via line 4 at the rate of 4 lbs per hr. This stream is condensed with tower water and removed from the system, the composition being mostly water. There is no reflux to the column.

The improvement in product quality (the purified product was free of malodor) was measured by comparing GC analysis of the vapor above liquid feed and purified product. This comparison showed that the GC chart area representing the impurities was reduced from 338 area units to 1 unit as a result of the treatment according to the invention.

From the above description it can be seen that practice of the invention provides a unique and successful method for conveniently purifying organic streams such as the di-propylene glycol n-butyl ether from lower boiling organic impurities without the necessity for the elaborate and extensive procedures which were used in the prior art, and without a significant loss of desirable product.

EXAMPLE 2

Although 1,3 methyl propanediol (MPD) of high purity (99%) is readily produced, frequently even this high purity material has madedorus contaminants.

In accordance with the invention, a liquid stream of MPD (99%) containing malodorus contaminants together with 5 wt % water was preheated to about 122–129° C. and fed at the rate of 150 cc/hr to the top of a 30 tray column. The column had 5 trays above the introduction point but these did not contribute to the distillation source as there was no column reflux.

Operation was analogous to that shown in the attached drawing except that both MPD and water were introduced via line 2, there was no feed via line 3.

Heat was provided by heating bottoms in reboiler 7 at 145° C. and returning vapors to column via line 8.

The column overhead at 100 mm Hg and 34–40° C. was removed at the rate of 5–15 cc/hr, condensed and passed to receiving vessel 5.

A product stream substantially free of malodorous contaminants was removed via line 11 at the rate of 120–140 cc/hr, a purge was removed via line 9 at the rate of 5–15 cc/hr.

The effectiveness of the invention was determined by comparing the results of the invention with those achieved by a conventional distillation procedure. By GC analysis, it was determined that impurities in MPD as normally produced were represented by 31100 area units. Conventional distillation reduced this to 5795 area units but resulted in an 18% loss of product. Practice of the invention as described above reduced the impurities to 1388 area units without significant product loss, thus demonstrating the effectiveness of the invention. The product of the invention was nearly odorless as compared to the starting material and the product of conventional distillation each of which had significant malodor.

I claim:

1. A process for separating minor impurities from a glycol which consists essentially of introducing a mixture of the glycol and impurities into a fractional distillation column having an upper and lower section at a feed point in the upper section of the column and introducing a stream of liquid water stripping component into said column at or below the glycol feed point, providing heat to the column by means of a bottoms reboiler in amount just sufficient to vaporize the stream of liquid water stripping component and account for heat losses, removing an overhead vapor stream comprised of substantially all of the introduced water stripping component together with at least a predominance of the impurities, removing a liquid bottoms stream comprised predominantly of the glycol and heating the bottoms to vaporize at least a portion thereof, returning a portion of the vaporized bottoms to provide sufficient heat to the column to vaporize the stream of liquid water stripping component, and recovering glycol reduced in impurities.

2. The process of claim 1 wherein the glycol purified is propylene glycol.

* * * * *